US 8,285,352 B2

(12) United States Patent
Addison et al.

(10) Patent No.: US 8,285,352 B2
(45) Date of Patent: Oct. 9, 2012

(54) SYSTEMS AND METHODS FOR IDENTIFYING PULSE RATES

(75) Inventors: Paul Stanley Addison, Edinburgh (GB); James Nicholas Watson, Dunfermline (GB)

(73) Assignee: Nellcor Puritan Bennett LLC, Boulder, CO (US)

( * ) Notice: Subject to any disclaimer, the term of this patent is extended or adjusted under 35 U.S.C. 154(b) by 1021 days.

(21) Appl. No.: 12/249,087

(22) Filed: Oct. 10, 2008

(65) Prior Publication Data
US 2010/0016693 A1    Jan. 21, 2010

Related U.S. Application Data

(60) Provisional application No. 61/080,782, filed on Jul. 15, 2008.

(51) Int. Cl.
*A61B 5/024* (2006.01)
*A61B 5/1455* (2006.01)
*G01J 3/433* (2006.01)
*G01N 33/48* (2006.01)

(52) U.S. Cl. ............. 600/324; 600/323; 356/41; 702/19

(58) Field of Classification Search .................. None
See application file for complete search history.

(56) References Cited

U.S. PATENT DOCUMENTS

| | | |
|---|---|---|
| 4,289,141 A | 9/1981 | Cormier |
| 4,911,167 A | 3/1990 | Corenman et al. |
| 4,934,372 A | 6/1990 | Corenman et al. |
| 5,439,483 A | 8/1995 | Duong-Van |
| RE35,122 E | 12/1995 | Corenman et al. |
| 5,590,650 A | 1/1997 | Genova |
| 5,632,272 A | 5/1997 | Diab et al. |
| 5,778,881 A | 7/1998 | Sun et al. |
| 5,795,304 A | 8/1998 | Sun et al. |
| 5,797,840 A | 8/1998 | Akselrod |
| 5,827,195 A | 10/1998 | Lander |
| 5,967,995 A | 10/1999 | Shusterman et al. |
| 6,002,952 A | 12/1999 | Diab et al. |
| 6,036,653 A | 3/2000 | Baba et al. |
| 6,094,592 A | 7/2000 | Yorkey |

(Continued)

FOREIGN PATENT DOCUMENTS

JP         09-084776        3/1997

(Continued)

OTHER PUBLICATIONS

Addison, Paul S., The Illustrated Wavelet Transform Handbook, Taylor & Francis Group, 2002.

(Continued)

*Primary Examiner* — Shanon A Foley

(57) ABSTRACT

According to embodiments, techniques for using continuous wavelet transforms and spectral transforms to identify pulse rates from a photoplethysmographic (PPG) signal are disclosed. According to embodiments, candidate pulse rates of the PPG signal may be identified from a wavelet transformed PPG signal and a spectral transformed PPG signal. A pulse rate may be determined from the candidate pulse rates by selecting one of the candidate pulse rates or by combining the candidate pulse rates. According to embodiments, a spectral transform of a PPG signal may be performed to identify a frequency region associated with a pulse rate of the PPG signal. A continuous wavelet transform of the PPG signal at a scale corresponding to the identified frequency region may be performed to determine a pulse rate from the wavelet transformed signal.

17 Claims, 11 Drawing Sheets

U.S. PATENT DOCUMENTS

| | | | |
|---|---|---|---|
| 6,095,984 | A | 8/2000 | Amano et al. |
| 6,117,075 | A | 9/2000 | Barnea |
| 6,129,675 | A | 10/2000 | Jay |
| 6,135,966 | A | 10/2000 | Ko |
| 6,171,257 | B1 | 1/2001 | Weil et al. |
| 6,171,258 | B1 | 1/2001 | Karakasoglu et al. |
| 6,208,951 | B1 | 3/2001 | Kumar et al. |
| 6,293,915 | B1 | 9/2001 | Amano et al. |
| 6,325,761 | B1 | 12/2001 | Jay |
| 6,361,501 | B1 | 3/2002 | Amano et al. |
| 6,393,311 | B1 | 5/2002 | Edgar, Jr. et al. |
| 6,561,986 | B2 | 5/2003 | Baura |
| 6,608,934 | B2 | 8/2003 | Scheirer |
| 6,650,917 | B2 | 11/2003 | Diab et al. |
| 6,654,623 | B1 | 11/2003 | Kastle |
| 6,699,194 | B1 | 3/2004 | Diab et al. |
| 6,745,060 | B2 | 6/2004 | Diab et al. |
| 6,810,277 | B2 | 10/2004 | Edgar, Jr. et al. |
| 6,850,787 | B2 | 2/2005 | Weber et al. |
| 6,931,269 | B2 | 8/2005 | Terry |
| 6,970,792 | B1 | 11/2005 | Diab |
| 7,001,337 | B2 | 2/2006 | Dekker |
| 7,020,507 | B2 | 3/2006 | Scharf |
| 7,035,679 | B2 * | 4/2006 | Addison et al. ............... 600/323 |
| 7,043,293 | B1 | 5/2006 | Baura |
| 7,054,453 | B2 | 5/2006 | Causevic |
| 7,054,454 | B2 | 5/2006 | Causevic et al. |
| 7,079,888 | B2 | 7/2006 | Oung |
| 7,171,269 | B1 | 1/2007 | Addison |
| 7,173,525 | B2 | 2/2007 | Albert |
| 7,203,267 | B2 | 4/2007 | De Man et al. |
| 7,225,013 | B2 | 5/2007 | Geva et al. |
| 7,254,500 | B2 | 8/2007 | Makeig |
| 7,289,835 | B2 | 10/2007 | Mansfield |
| 7,373,194 | B2 | 5/2008 | Weber et al. |
| 7,515,949 | B2 | 4/2009 | Norris |
| 7,519,488 | B2 | 4/2009 | Fu |
| 7,523,011 | B2 | 4/2009 | Akiyama et al. |
| 2003/0036685 | A1 * | 2/2003 | Goodman ............... 600/300 |
| 2003/0163057 | A1 | 8/2003 | Flick et al. |
| 2005/0043616 | A1 | 2/2005 | Chinchoy |
| 2006/0209631 | A1 | 9/2006 | Melese et al. |
| 2006/0211930 | A1 | 9/2006 | Scharf et al. |
| 2006/0229519 | A1 | 10/2006 | Fujiwara et al. |
| 2006/0258921 | A1 | 11/2006 | Addison et al. |
| 2006/0265022 | A1 | 11/2006 | John et al. |
| 2007/0021673 | A1 | 1/2007 | Arbel et al. |
| 2007/0073120 | A1 | 3/2007 | Li et al. |
| 2007/0073124 | A1 | 3/2007 | Li et al. |
| 2007/0167694 | A1 | 7/2007 | Causevic et al. |
| 2007/0167851 | A1 | 7/2007 | Vitali et al. |
| 2007/0282212 | A1 | 12/2007 | Sierra et al. |
| 2008/0045832 | A1 | 2/2008 | McGrath |
| 2008/0082018 | A1 | 4/2008 | Sackner et al. |
| 2008/0214903 | A1 | 9/2008 | Orbach |
| 2008/0243021 | A1 | 10/2008 | Causevic et al. |

FOREIGN PATENT DOCUMENTS

| | | |
|---|---|---|
| WO | WO 01/25802 | 4/2001 |
| WO | WO 01/62152 | 8/2001 |
| WO | WO 03/055395 | 7/2003 |
| WO | WO 2004/075746 | 9/2004 |
| WO | WO 2004/105601 | 12/2004 |
| WO | WO 2005/096170 | 10/2005 |
| WO | WO 2006/085120 | 8/2006 |

OTHER PUBLICATIONS

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Application," Journal of the Institute of Electronics, Information and Communication Engineers, vol. 76, No. 5, May 1993, pp. 518-528.

* cited by examiner

SYSTEMS AND METHODS FOR IDENTIFYING PULSE RATES

CROSS-REFERENCE TO RELATED APPLICATION

This application claims the benefit of U.S. Provisional Application No. 61/080,782, filed Jul. 15, 2008, which is hereby incorporated by reference herein in its entirety.

SUMMARY

The present disclosure relates to signal processing and, more particularly, the present disclosure relates to using continuous wavelet transforms and spectral transforms to identify pulse rates from a photoplethysmographic (PPG) signal.

The known advantages of the Continuous Wavelet Transform (CWT), inherent resolution in both scale and time, may be advantageous in identifying and characterizing features within a signal. Repeating features with a changing periodicity, such as the pulse rate, may be tracked in time using CWTs. An estimate of the periodicity of such features may also be achieved using spectral techniques. Pulse rate periodicity may be calculated most accurately and efficiently by using the strengths of the CWT in conjunction with the Fourier transform.

For example, a spectral transform may be used to quickly identify frequency regions of a signal likely to be the pulse rate. The CWT may then focus on these regions to determine or filter the actual pulse rate through time. For example, a Fourier transform may be employed using standard peak-picking techniques (e.g., selecting maxima turning points), to identify nominal frequency(s) of interest for identification of pulse rate. The CWT may then be performed at scales with characteristic frequencies at and around these frequencies of interest. The maxima ridges in the scalogram proximal to these scales (corresponding to these frequencies of interest) may then be used to identity the actual pulse rate. The CWT technique may provide a more accurate calculation of the pulse rate due to its ability to track changes in pulse rate (changes in the frequency of interest) through time and its ability to ignore regions of scalogram associated with temporally discrete artifacts (e.g., spikes). Both these features are due to the CWT's ability to better resolve in the time domain when compared to spectral averaging techniques.

Alternatively, pulse rates may be calculated using both the spectral (e.g., frequency of highest value spectral peak) and CWT (e.g., characteristic frequency of scale with highest value maxima ridge) techniques with the two results combined by, for example taking an average or weighted average to obtain an improved value for the calculated pulse rate.

Alternatively pulse rates may be calculated using both the spectral and CWT techniques and one of the results may be selected such as the one which is closest to an expected (e.g., historical) value to obtain an improved value for the calculated pulse rate.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
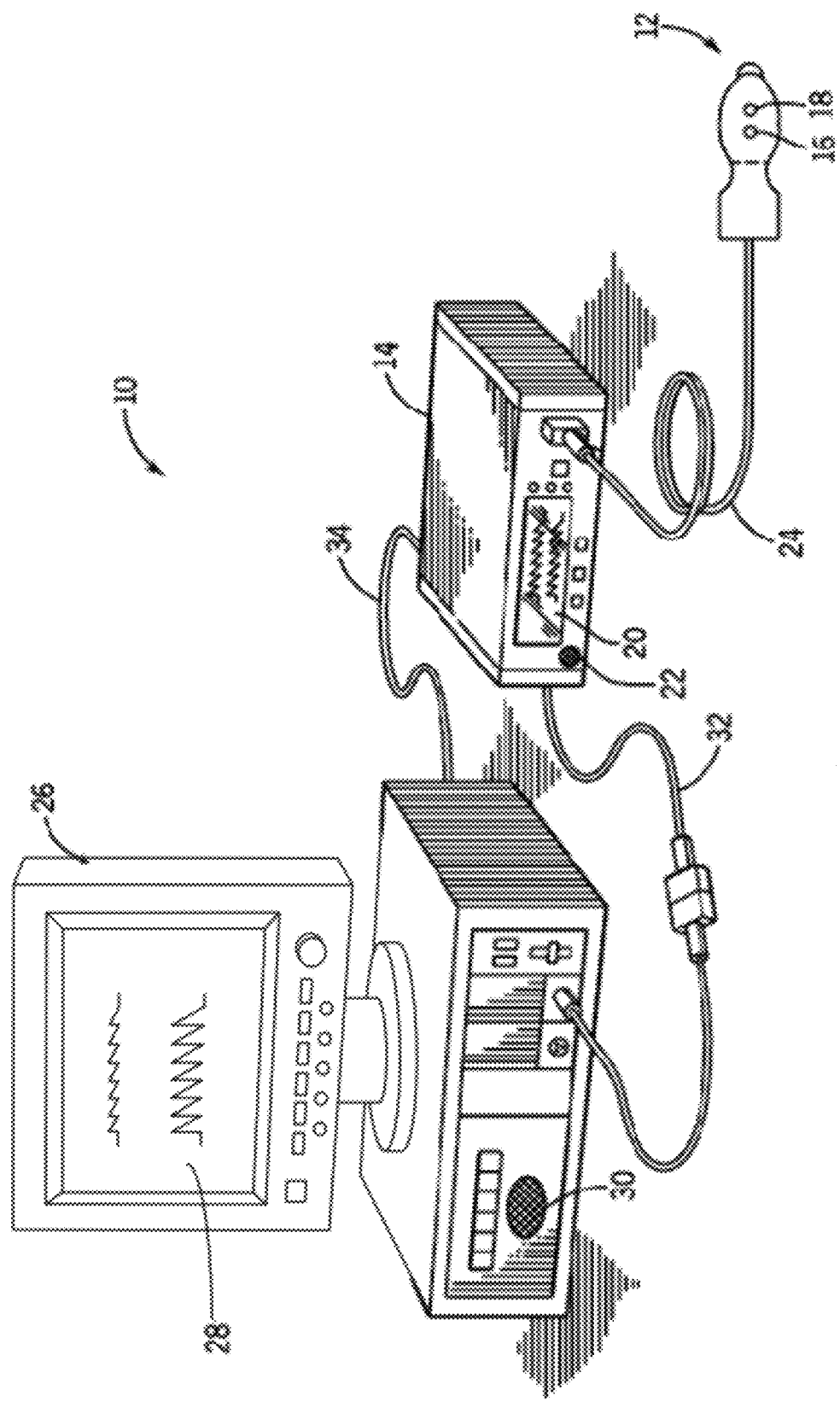
FIG. 1 shows an illustrative pulse oximetry system in accordance with an embodiment.

In medicine, a plethysmograph is an instrument that measures physiological parameters, such as variations in the size of an organ or body part, through an analysis of the blood passing through or present in the targeted body part, or a depiction of these variations. An oximeter is an instrument that may determine the oxygen saturation of the blood. One common type of oximeter is a pulse oximeter, which determines oxygen saturation by analysis of an optically sensed plethysmograph.

A pulse oximeter is a medical device that may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t) = I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A-log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t) = [I(t_2, \lambda_{IR}) - I(t_1, \lambda_{IR})]I(t_1, \lambda_R)$$

$$y(t) = [I(t_2, \lambda_R) - I(t_1, \lambda_R)]I(t_1, \lambda_{IR})$$

$$y(t) = Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to an embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
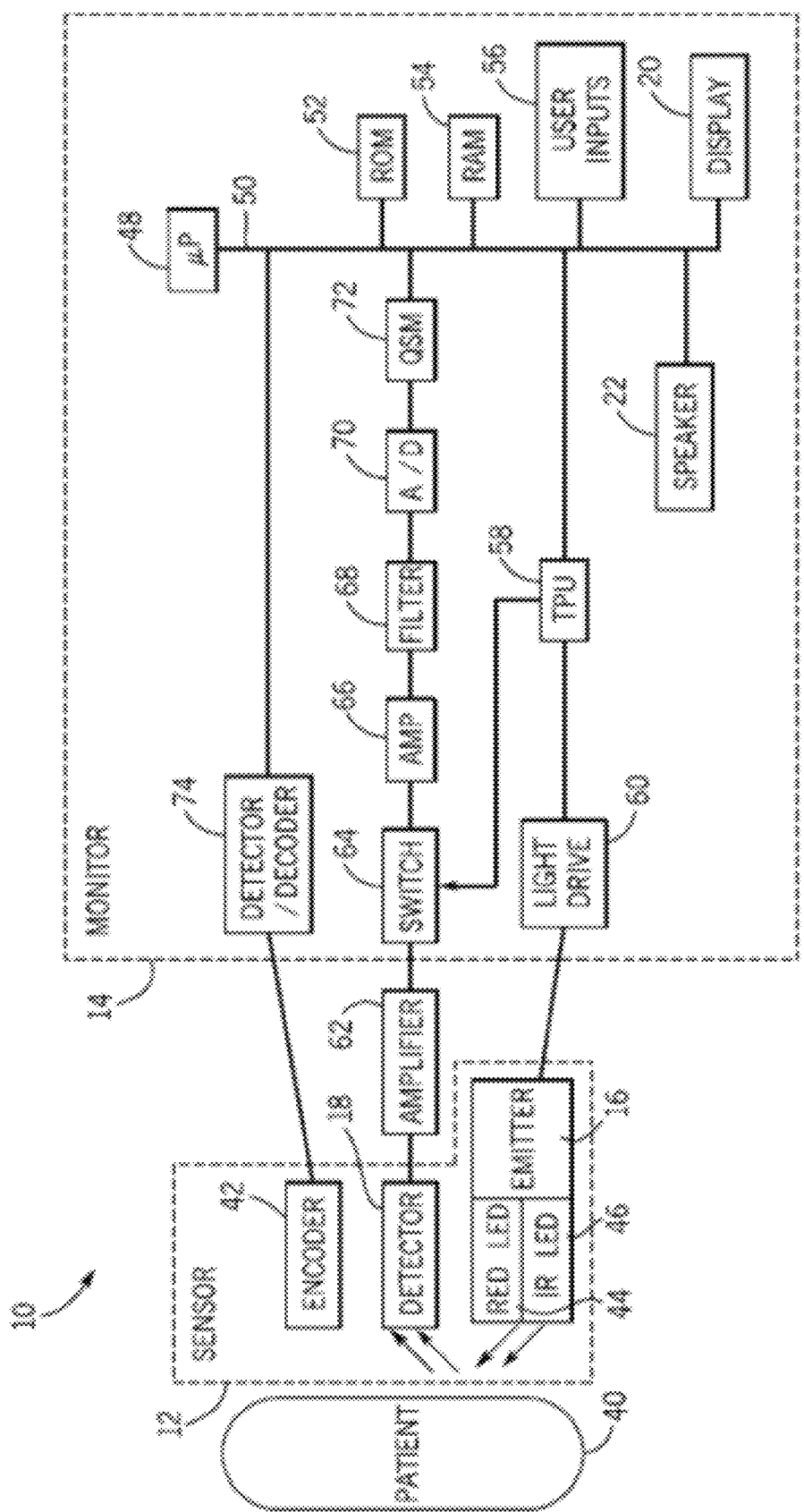
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a,b) = \frac{1}{\sqrt{a}} \int_{-\infty}^{+\infty} x(t)\psi^*\left(\frac{t-b}{a}\right)dt \qquad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \qquad (10)$$

where '||' is the modulus operator. The scalogram may be rescaled for useful purposes. One common rescaling is defined as $$S_R(a, b) = \frac{|T(a, b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \qquad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{j2\pi f_0 t} - e^{-(2\pi f_0)^2/2})e^{-t^2/2} \qquad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \tag{14}$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
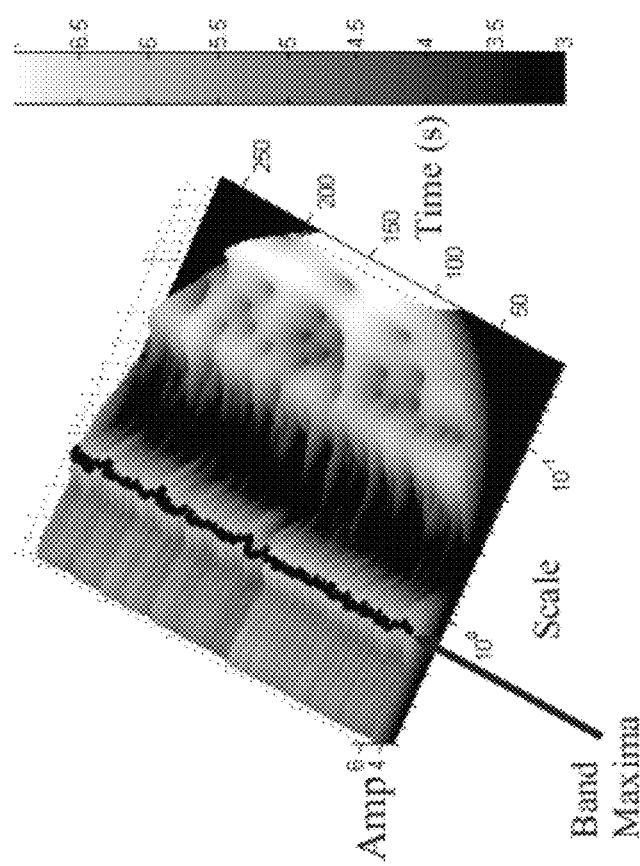
FIGS. 3(a) and 3(b) show illustrative views of a scalogram derived from a PPG signal in accordance with an embodiment.
Figure 3A:
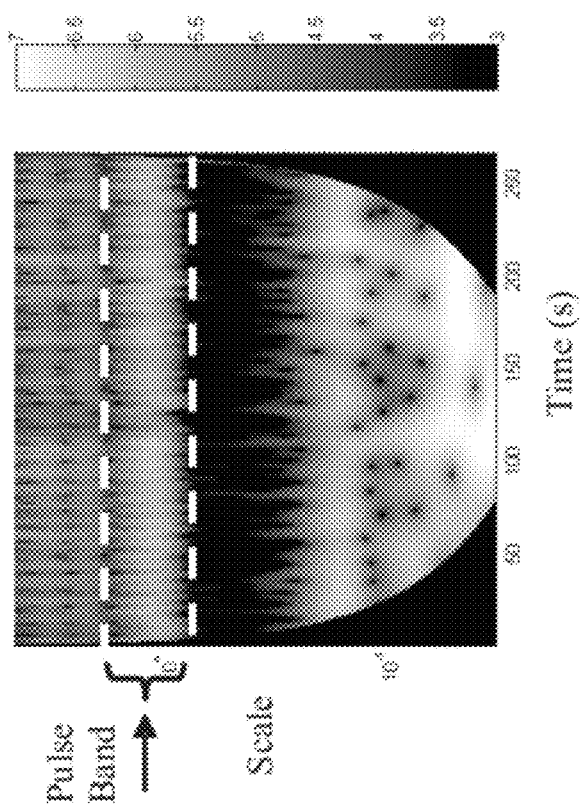

Pertinent repeating features in a signal give rise to a time-scale band in wavelet space or a resealed wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable resealing of the scalogram, such as that given in equation (11), the ridges found in wavelet space may be related to the instantaneous frequency of the signal. In this way, the pulse rate may be obtained from the PPG signal. Instead of resealing the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
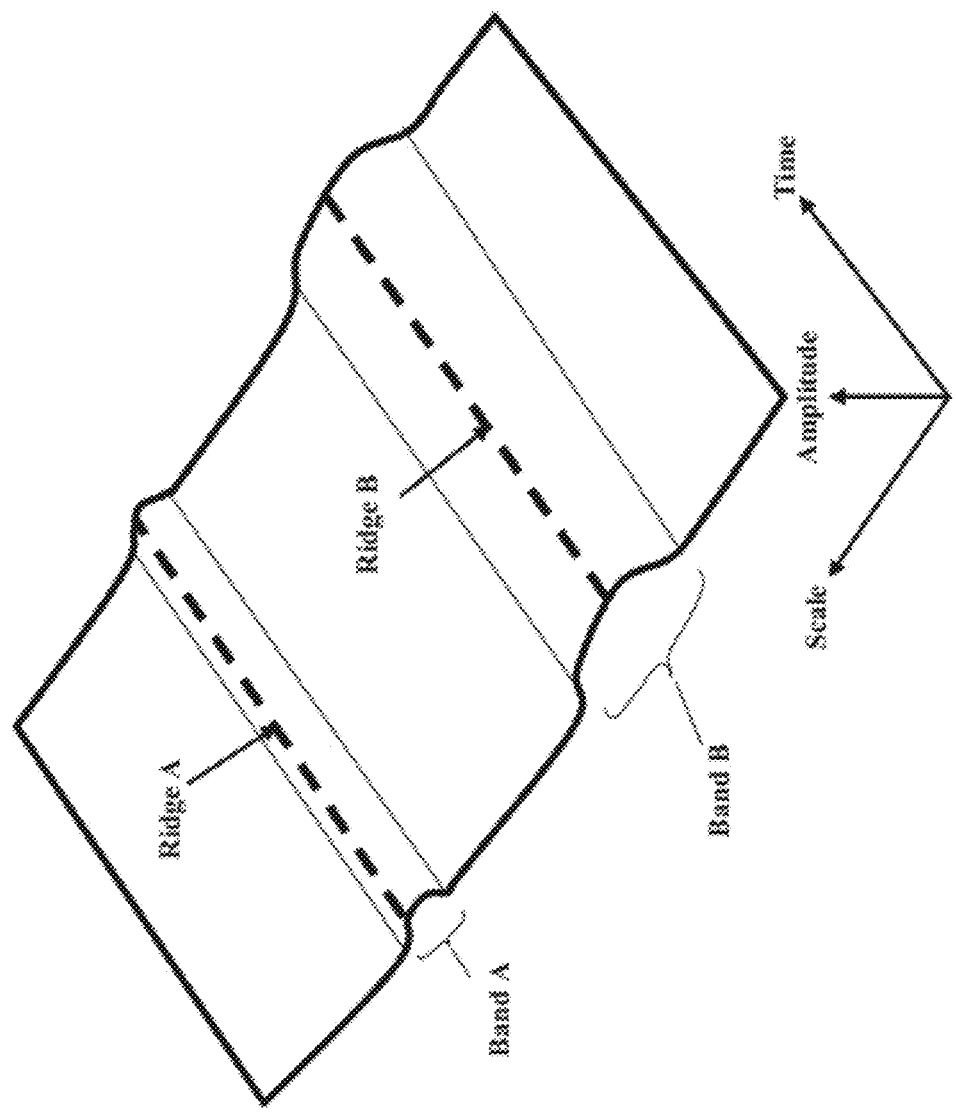
FIG. 3(c) shows an illustrative scalogram derived from a signal containing two pertinent components in accordance with an embodiment.
Figure 3D:
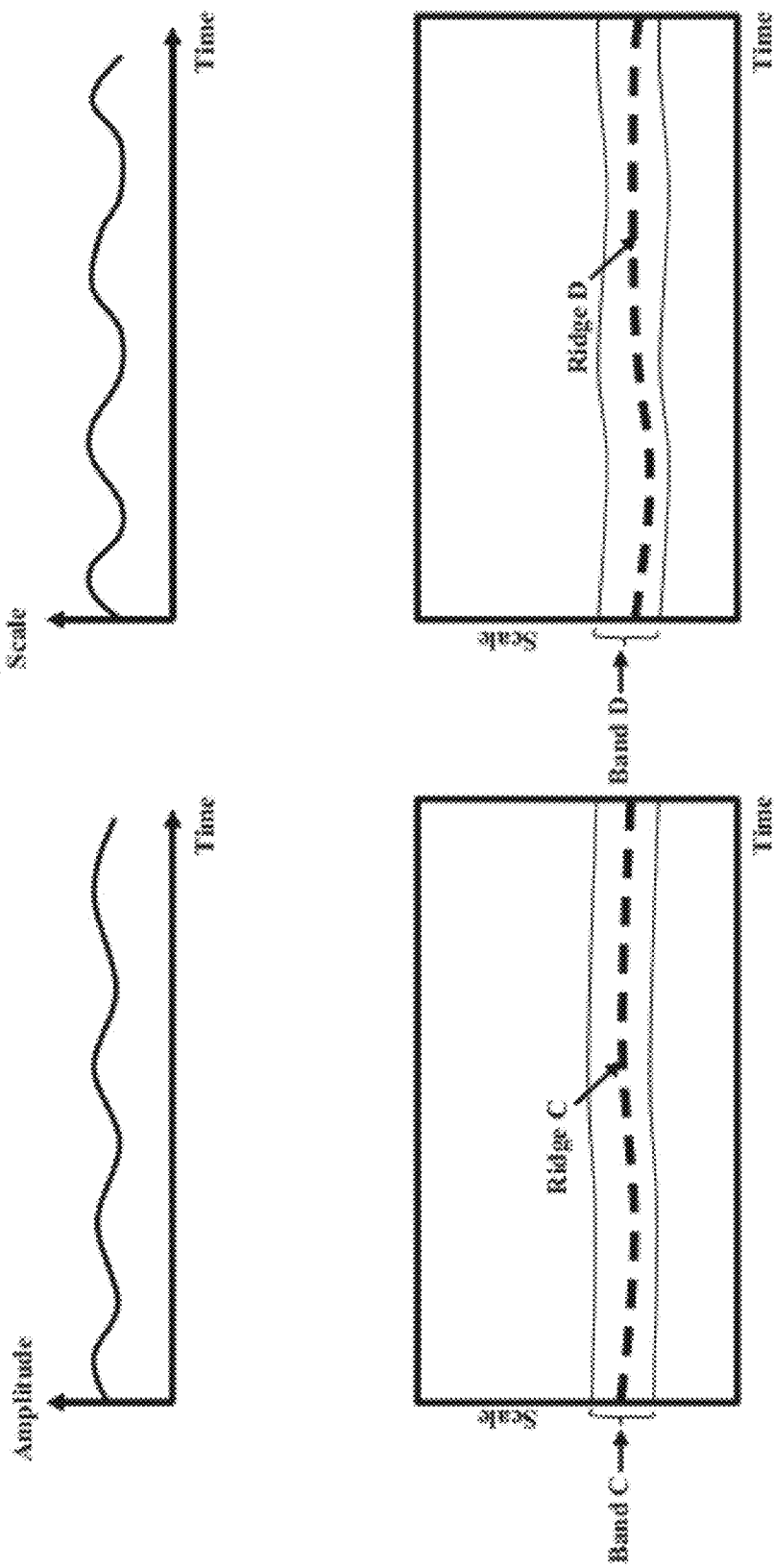
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a resealed wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\, db}{a^2} \tag{15}$$

which may also be written as:

$$x(t) = \frac{1}{C_g} \int_{-\infty}^{\infty} \int_0^{\infty} T(a,b) \psi_{a,b}(t) \frac{da\, db}{a^2} \tag{16}$$

where $C_g$ is a scalar value known as the admissibility constant. It is wavelet type dependent and may be calculated from:

$$C_g = \int_0^{\infty} \frac{|\hat{\psi}(f)|^2}{f} df \tag{17}$$

Figure 3E:
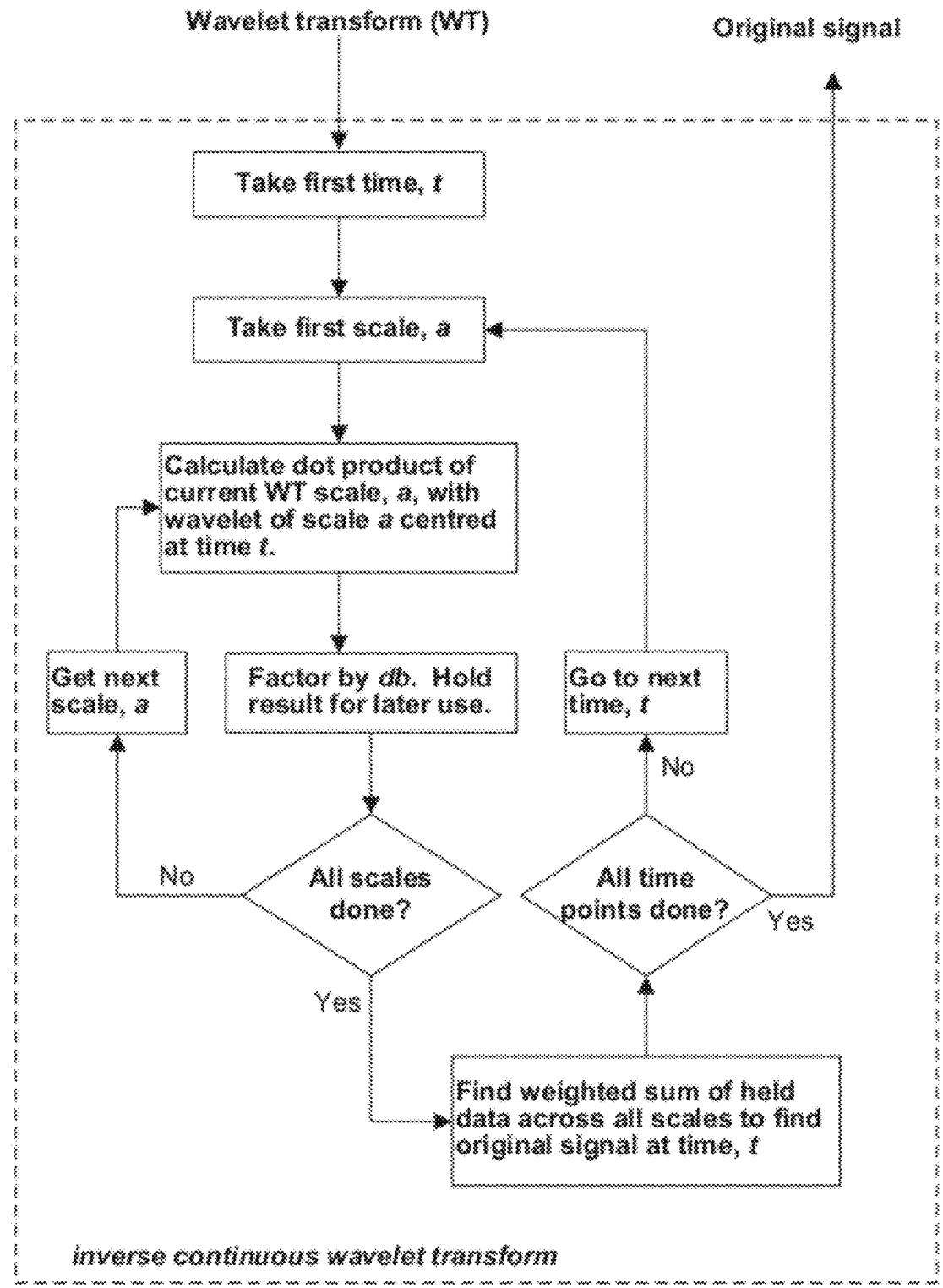
FIGS. 3(e) and 3(f) are flow charts of illustrative steps involved in performing an inverse continuous wavelet transform in accordance with embodiments.
Figure 3F:
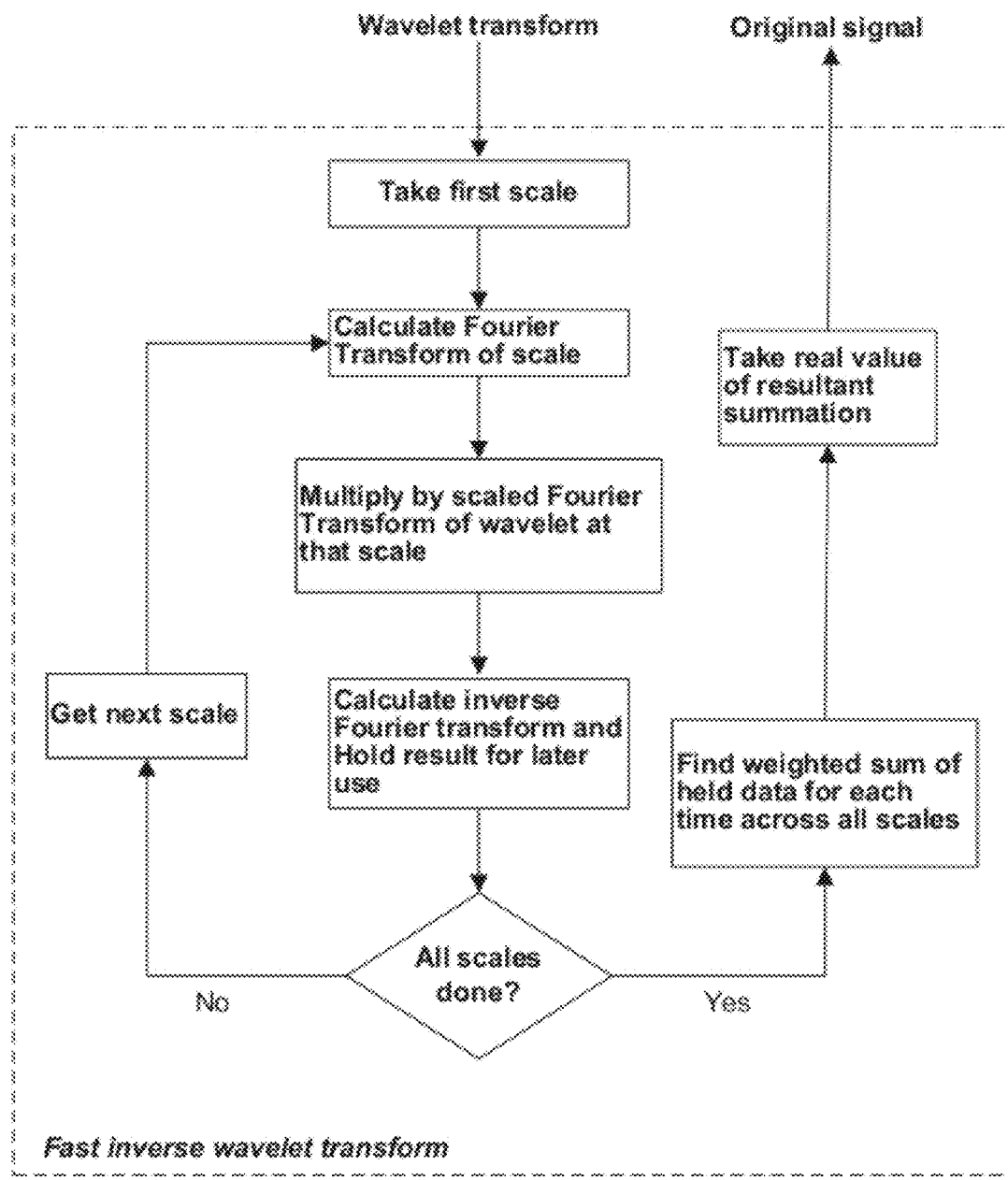

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
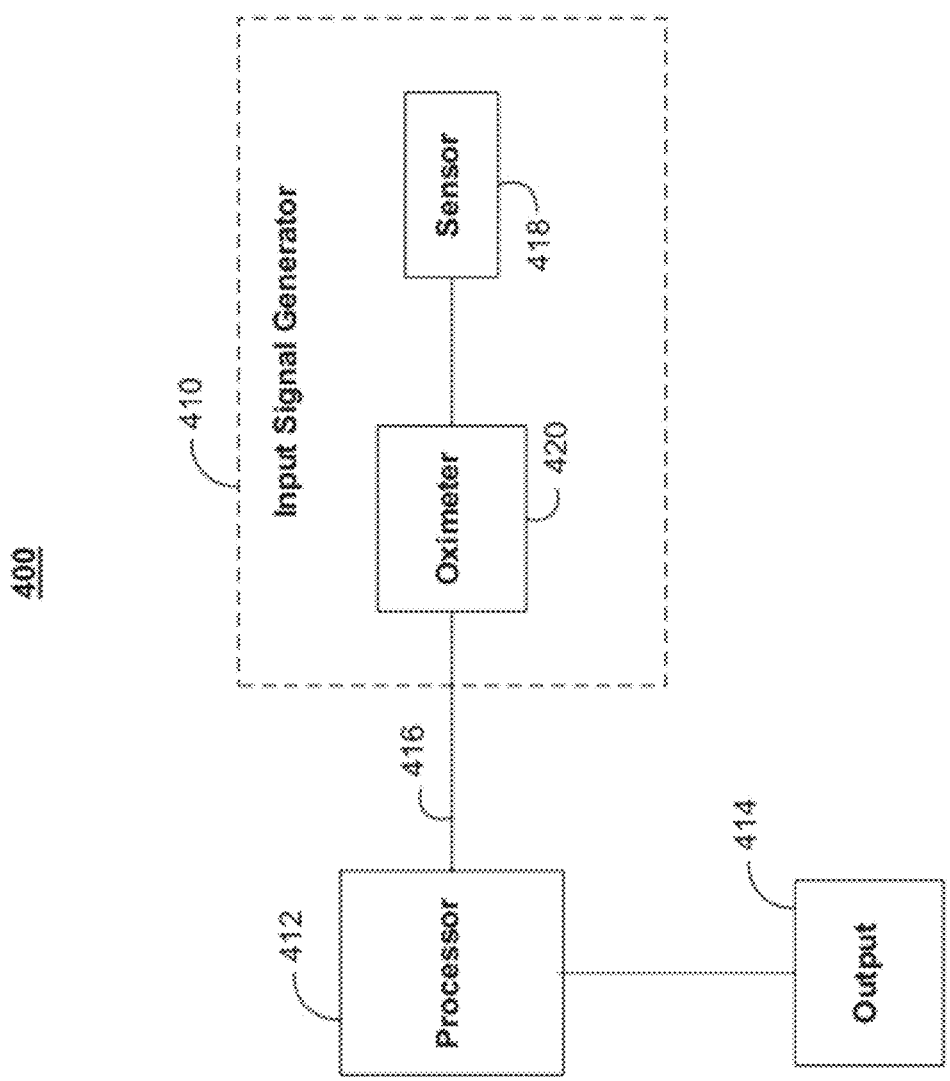
FIG. 4 is a block diagram of an illustrative continuous wavelet processing system in accordance with some embodiments.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Figure 5:
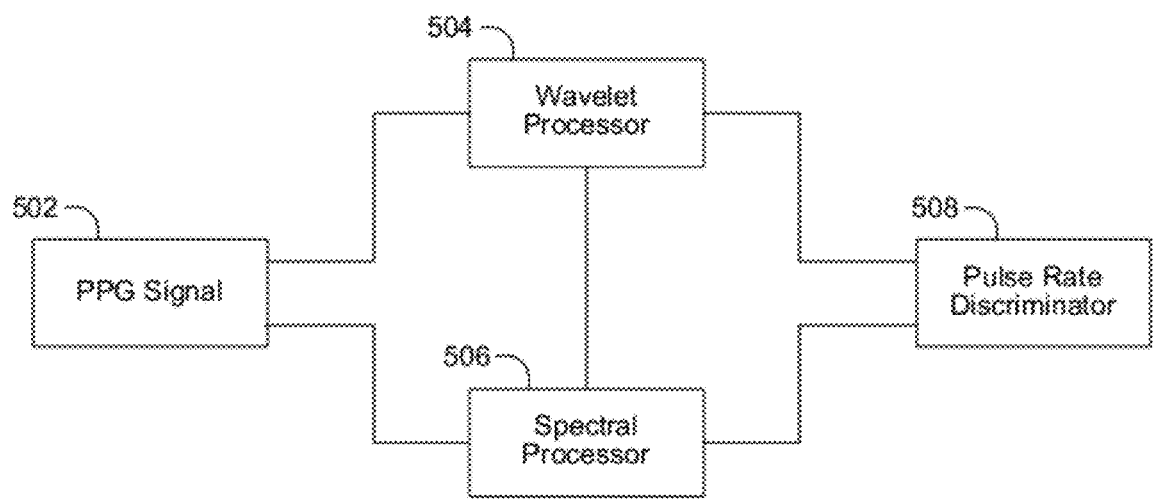
FIG. 5 shows an illustrative schematic of a system for determining a pulse from a PPG signal in accordance with some embodiments.

FIG. 5 shows an illustrative system 500 in which pulse rate discriminator 508 may determine a pulse rate from PPG signal 502. Candidate pulse rates may be identified from PPG signal 502 using wavelet processor 504 and/or spectral processor 506. Pulse rate discriminator 508 may determine the pulse rate by selecting one of the candidate pulse rates or by combining the candidate pulse rates. System 500 may be implemented within continuous wavelet processing system 400 (FIG. 4) or within any other suitable systems.

Wavelet processor 504 may perform one or more continuous wavelet transforms of PPG signal 502 in accordance with the present disclosure to identify a candidate pulse rate. Wavelet processor 504 may generate scalograms from PPG signal 502 and analyze the scalograms to identify bands of scales that correspond to a pulse rate of PPG signal 502. As described above, a scalogram generated from a continuous wavelet transform of a PPG signal generally contains a band of scales corresponding to the pulse components of the PPG signal, a band of scales corresponding to the breathing components of the PPG signal, and one or more other bands of scales that correspond other components such as noise and artifacts. These bands may be used to identify and characterize the repeating features of the PPG signal and may be used to track changes in the frequencies of these features over time. In some embodiments, wavelet processor 504 may reduce or remove the bands of scales from the scalogram that do not correspond to the pulse components.

As discussed above, a value for the pulse rate identified from the band of scales corresponding to the pulse components of PPG signal 502 may be obtained by employing a suitable rescaling of the scalogram such that the ridges found in wavelet space may be related to the instantaneous frequency of PPG signal 502. Instead of rescaling the scalogram, a suitable predefined relationship between the scale obtained from the ridge on the wavelet surface and the actual pulse rate may also be used to determine the pulse rate.

In some embodiments, wavelet processor 504 may filter PPG signal 502 using one or more suitable filters (not shown) to reduce noise or artifacts present in PPG signal 502. Wavelet processor 504 may filter PPG signal 502 before, after, or in-between performing the one or more continuous wavelet transforms. Furthermore, the one or more filters may also be used to reduce features within PPG signal 502 that do not contain pulse rate information. For example, a band-pass filter may be applied to PPG signal 502 to attenuate frequency components outside of a frequency range associated with potential pulse rates. Generating a scalogram by performing one or more continuous wavelet transforms on a filtered PPG signal may enhance the band of scales corresponding to the pulse components while preferably reducing or eliminating other bands of scales. As used herein, the term "filter" shall refer to any suitable type of filter or processor capable of filtering or processing a signal to either generate a filtered signal or to extract data from the signal.

Spectral processor 504 may also be used in accordance with the present disclosure to identify a candidate pulse rate from PPG signal 502. Spectral processor 504 may perform one or more spectral transforms on PPG signal 502 in order to transform the PPG signal from the time-domain into a frequency domain representation of the PPG signal. Any suitable spectral transform functions or combination of spectral transform functions may be used by spectral processor 504 including, for example, continuous Fourier transforms, discreet Fourier transforms, fast Fourier transforms (FFT), and forward Fourier transforms. In fact, any suitable frequency transform function may be used. The transformed PPG signal represents an amplitude of the signal as a function of frequency. Pertinent repeating features in PPG signal 502 give rise to peaks within the transformed PPG signal corresponding to the frequency of occurrence of those features. Accordingly, the pulse component of PPG signal 502 produces a peak in the transformed PPG signal at or around the pulse frequency. Once the pulse frequency is identified, it may be easily converted into a pulse rate. Other components of PPG signal 502 including breathing components of the PPG signal as well as noise or artifacts may also produce peaks in the transformed PPG signal.

Spectral processor 506 may identify a candidate pulse rate of PPG signal 502 by determining the frequency of the largest peak in the transformed PPG signal. In other embodiments, spectral processor 506 may select between several peaks in the transformed PPG signals. This selection may be made based on an expected frequency of the pulse components of PPG signal 502. Further, the selection may be made by comparing the relative frequencies and amplitudes of the various peaks. In addition, performing additional frequency transforms on PPG signal 502 may increase the size of the peak associated with pulse components of PPG signal 502 relative to the other peaks and may make it easier to select the correct peak as the pulse peak.

Spectral processor 506 may filter PPG signal 502 using one or more suitable filters (not shown) before, after, or in-between performing the one or more spectral transforms to reduce noise or artifacts present in PPG signal 502. Furthermore, the one or more filters may also be used to reduce features within PPG signal 502 that do not contain pulse rate information. Filtering the PPG signal in this manner may enhance the peaks in the transformed PPG signal corresponding to the pulse components while preferably reducing or eliminating other peaks. It should be understood that spectral processor 506 may share one or more filters with Wavelet processor 504.

Pulse rate discriminator 508 may determine a pulse rate value from PPG signal 502 based on the candidate pulse rates identified by wavelet processor 504 and spectral processor 506. Pulse rate discriminator 508 may compare the pulse rate candidates identified by wavelet processor 504 and spectral processor 506. If wavelet processor 504 and spectral processor 506 identify pulse rate candidates that differ by more that a predetermined amount, only one of candidate pulse rates may be selected by pulse rate discriminator 508 as the determined pulse rate. For example, the selected pulse rate candidate may be the pulse rate candidate with a more likely value, with a more stable value, or with a value closer to a previously determined pulse rate. Alternatively, when the pulse rate candidates differ by more that a predetermined amount, pulse rate discriminator 508 may select a pulse rate candidate based on its source. For example, a pulse rate candidate identified by wavelet processor 504 may be given precedence over a pulse rate candidate identified by spectral processor 506 or vise versa.

In one embodiment, peaks and ridges found by the spectral and wavelet processors may be used by pulse rate discriminator 508 (i.e., as opposed to or in addition to candidate rates). For example, pulse rate discriminator 508 may compare peak positions in the spectral spectrum with ridge shapes in the scalogram to see if one supports the other. It will be understood that a ridge can change scale with time and may potentially not be just one pulse rate but a set of pulse rates over time.

If the pulse rate candidates identified by wavelet processor 504 and spectral processor 506 differ by less than a predetermined amount, the pulse rate candidates may be combined to generate the determined pulse rate. The combined pulse rate may be an average or a weighted average of the two pulse rate values. Alternatively, when both pulse rates differ by less than a predetermined amount, pulse rate discriminator 508 may select only one of the candidate pulse rates. Similar to the previous scenario, the candidate pulse rate may be selected based on the value of the candidate pulse rate or the source of the candidate pulse rate.

Wavelet processor 504 and spectral processor 506 may provide confidence values associated with their respective candidate pulse rates. A high confidence value may reflect a greater accuracy in identifying a candidate pulse rate, while a low confidence value may reflect a lower accuracy. For example, the confidence value generated by wavelet processor 504 may be determined based on the quality the band of scales corresponding to the pulse components of the PPG signal and the presence, proximity, and quality of other bands of scales. Similarly, the confidence value generated by spectral processor 506 may be determined based on the value of the peak corresponding to the pulse components of the PPG signal and the presence, proximity, and values of other peaks. Pulse rate discriminator 508 may compare the confidence values associated with the candidate pulse rates. In some embodiments, pulse rate discriminator 508 may select the candidate with the higher confidence value. In some other embodiments, pulse rate discriminator 508 may combine the two candidate pulse rates by giving the candidate pulse rates weights that are based on at least in part on their confidence values.

Whereas wavelet processor 504 and spectral processor 506 have been described herein as identifying candidate pulse rate values independently, it should be understood that information may be passed between wavelet processor 504 and spectral processor 506 in order to improve the accuracy and/or speed of pulse rate identification. For example, spectral processor 506 may identify one or more frequencies of interest within a PPG signal for identification of pulse rate. Wavelet processor 504 may perform continuous wavelet transforms at scales with characteristic frequencies around these frequencies of interest. The maxima ridges in a scalogram proximal to these scales (corresponding to these frequencies of interest) may then be used to identify the actual pulse rate. Wavelet processor 504, using continuous wavelet transform techniques may provide a more accurate calculation of the pulse rate due to its ability to track changes in the pulse rate (changes in the frequency of interest) through time and its ability to ignore regions of the scalogram associated with temporally discrete artifacts (e.g., spikes). Both these features are due to the CWT's ability to better resolve in the time domain when compared to spectral averaging techniques. In other embodiments, wavelet processor 504 may provide a scale or rate identified from a continuous wavelet transform of a PPG signal to spectral processor 506 in order to help spectral processor 506 select the correct frequency peak for pulse rate determination.

Figure 6:
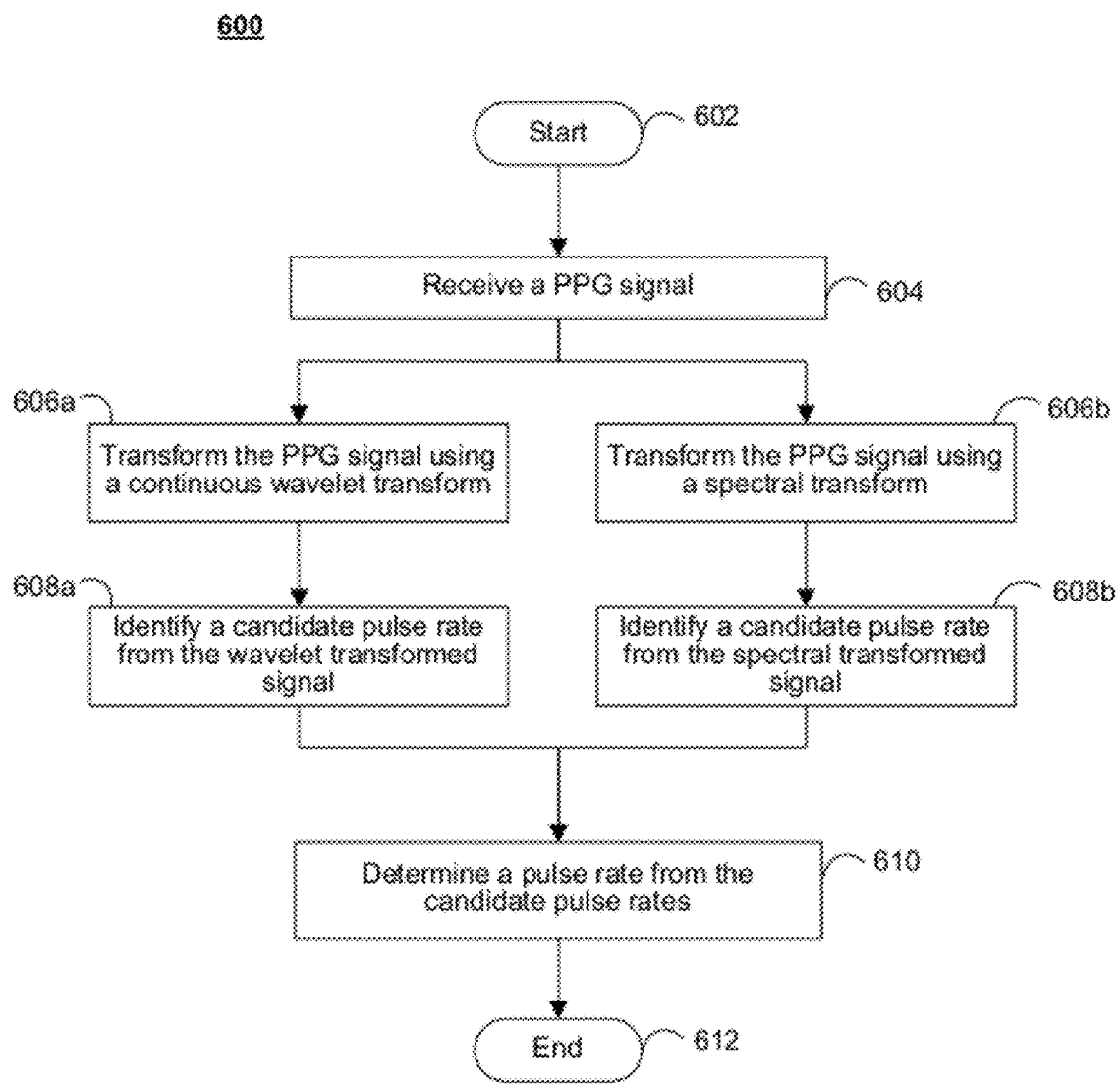
FIG. 6 is a flowchart of an illustrative process for identifying pulse rates from a PPG signal using continuous wavelet transforms and spectral transforms.

FIG. 6 is a flowchart of an illustrative process for identifying pulse rates from a PPG signal using continuous wavelet transforms and spectral transforms. Process 600 may begin at step 602. At step 604, a PPG signal is received. At step 606a, the PPG signal may be transformed using a continuous wavelet transform. At step 606b, the PPG signal may be transformed using a spectral transform. Then, at step 608a a candidate pulse rate may be identified from the wavelet transformed signal and at step 608b a candidate pulse rate may be identified from the spectral transformed signal. While steps 606a-608a and 606b-608b are illustrated as being performed substantially in parallel (e.g., by wavelet processor 504 and spectral processor 506 (FIG. 5)), it should be understood that these steps may also be performed serially. At step 610, a pulse rate may be determined from the candidate pulse rates identified from the wavelet transformed signal and from the spectral transformed signal at steps 608a and 608b, respectively. As discussed above with respect to pulse rate discriminator 508, a pulse rate may be determined by selecting one of the two candidate pulse rates or by combining both of the candidate pulse rates. Process 600 may then advance to step 612 and end.

Figure 7:
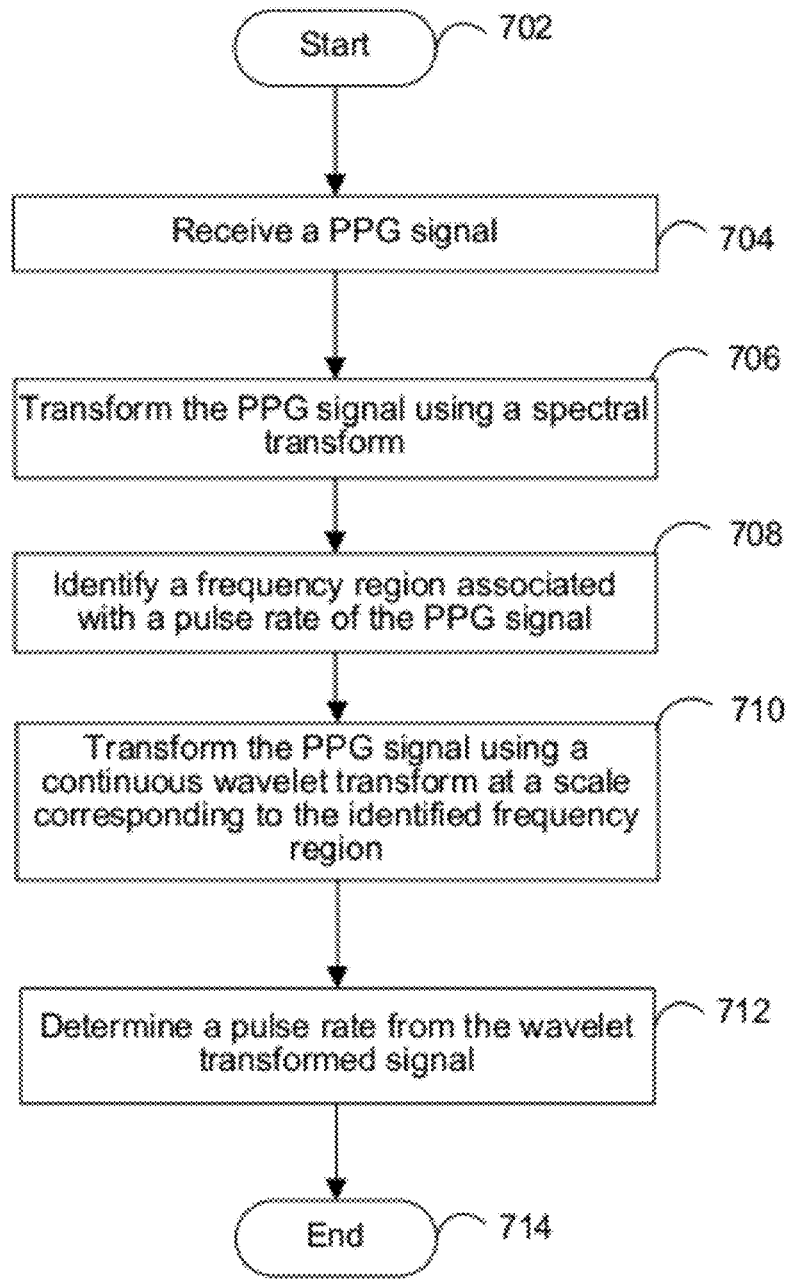
FIG. 7 is a flowchart of another illustrative process for identifying pulse rates from a PPG signal using continuous wavelet transforms and spectral transforms.

FIG. 7 is a flowchart of another illustrative process for identifying pulse rates from a PPG signal using continuous wavelet transforms and spectral transforms. Process 700 may begin at step 702. At step 704, a PPG signal is received. At step 706, the PPG signal may be transformed using a spectral transform. At step 708 a frequency region associated with a pulse rate of the PPG signal is identified. For example, spectral processor 506 (FIG. 5) may identify one or more frequency regions of interest within the PPG signal for identification of pulse rate. At step 710 the PPG signal may be transformed using a continuous wavelet transform at a scale corresponding to the identified frequency regions and at step 712 a pulse rate may be determined from the wavelet transformed signal. For example, Wavelet processor 504 (FIG. 5) may provide a more accurate calculation of the pulse rate using the frequency regions of interest provided by spectral processor 506. Process 700 may then advance to step 712 and end.

The foregoing is merely illustrative of the principles of this disclosure and various modifications can be made by those skilled in the art without departing from the scope and spirit of the disclosure. The following numbered paragraphs may also describe various aspects of the disclosure.

What is claimed is:

1. A method for determining a pulse rate from a photoplethysmographic (PPG) signal, comprising:
   using a processor for:
   receiving a PPG signal;
   performing a continuous wavelet transform of the PPG signal to produce a wavelet transformed signal;
   performing a spectral transform of the PPG signal to produce a spectrum;
   identifying a first candidate pulse rate of the PPG signal from the wavelet transformed signal;
   identifying a second candidate pulse rate of the PPG signal from the spectrum; and
   determining a pulse rate from the first candidate pulse rate and the second candidate pulse rate.

2. The method of claim 1 wherein the spectral transform comprises a Fourier transform.

3. The method of claim 1 wherein determining the pulse rate from the first candidate pulse rate and the second candidate pulse rate comprises selecting one of the candidate pulse rates.

4. The method of claim 3 wherein selecting one of the candidate pulse rates comprises selecting the candidate pulse rate based at least in part on its source.

5. The method of claim 3 wherein selecting one of the candidate pulse rates comprises selecting the candidate pulse rate based at least in part on its value.

6. The method of claim 3 further comprising determining confidence values associated with each of the first and the second candidate pulse rates and wherein selecting one of the candidate pulse rates comprises selecting the candidate pulse rate based at least in part on the confidence values.

7. The method of claim 1 wherein determining the pulse rate from the first candidate pulse rate and the second candidate pulse rate comprises combining the candidate pulse rates.

8. The method of claim 7 further comprising determining confidence values associated with each of the first and the second candidate pulse rates and wherein combining the candidate pulse rates comprises combining the candidate pulse rates weighted by the confidence values.

9. A system for determining a pulse rate from a photoplethysmographic (PPG) signal, comprising:
   a wavelet processor capable of performing a continuous wavelet transform of a received PPG signal to produce a wavelet transformed signal and identifying a first candidate pulse rate of the PPG signal from the wavelet transformed signal;
   a spectral processor capable of performing a spectral transform of the received PPG signal to produce a spectrum and identifying a second candidate pulse rate of the PPG signal from the spectrum; and
   a pulse rate discriminator capable of determining a pulse rate from the first candidate pulse rate and the second candidate pulse rate.

10. The system of claim 9 wherein the spectral transform comprises a Fourier transform.

11. The system of claim 9 wherein the pulse rate discriminator is capable of selecting one of the candidate pulse rates.

12. The system of claim 11 wherein the pulse rate discriminator is capable of selecting one of the candidate pulses based at least in part on its source.

13. The system of claim 11 wherein the pulse rate discriminator is capable of selecting one of the candidate pulses based at least in part on its value.

14. The system of claim 11 wherein the wavelet processor and the Fourier processor are capable of determining confidence values associated the first and the second candidate pulse rates and wherein the pulse rate discriminator is capable of selecting one of the candidate pulse rates based at least in part on the confidence values.

15. The system of claim 9 wherein the pulse rate discriminator is capable of combining the candidate pulse rates.

16. The system of claim 15 wherein the wavelet processor and the spectral processor are capable of determining confidence values associated the first and the second candidate pulse rates and wherein the pulse rate discriminator is capable of combining the pulse rate candidates weighted by the confidence values.

17. Computer-readable medium for use in determining a pulse rate from a photoplethysmographic (PPG) signal, the computer-readable medium having computer program instructions recorded thereon, wherein the computer program instructions, when executed on a processor, cause the processor to:

perform a continuous wavelet transform of a PPG signal to produce a wavelet transformed signal;

perform a spectral transform of the PPG signal to produce a spectrum;

identify a first candidate pulse rate of the PPG signal from the wavelet transformed signal;

identify a second candidate pulse rate of the PPG signal from the spectrum; and determine a pulse rate from the first candidate pulse rate and the second candidate pulse rate.

* * * * *